US009474810B2

(12) United States Patent
Hay et al.

(10) Patent No.: US 9,474,810 B2
(45) Date of Patent: *Oct. 25, 2016

(54) SUPERPARAMAGNETIC NANOPARTICLES WITH PEG SUBSTITUTED α-HYDROXY PHOSPHONATE SHELLS

(75) Inventors: Bruce Allan Hay, Niskayuna, NY (US); Daniel Eugene Meyer, Clifton Park, NY (US); Brian Christopher Bales, Niskayuna, NY (US); Michael Todd Luttrell, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 187 days.

This patent is subject to a terminal disclaimer.

(21) Appl. No.: 13/411,004

(22) Filed: Mar. 2, 2012

(65) Prior Publication Data

US 2013/0230463 A1 Sep. 5, 2013

(51) Int. Cl.
| | | |
|---|---|---|
| *A61K 49/18* | (2006.01) | |
| *A61K 47/48* | (2006.01) | |
| *A61K 33/26* | (2006.01) | |
| *A61K 33/28* | (2006.01) | |
| *A61K 33/24* | (2006.01) | |
| *A61K 33/32* | (2006.01) | |
| *A61K 33/34* | (2006.01) | |

(52) U.S. Cl.
CPC ............. *A61K 49/186* (2013.01); *A61K 33/24* (2013.01); *A61K 33/26* (2013.01); *A61K 33/32* (2013.01); *A61K 33/34* (2013.01); *A61K 47/48084* (2013.01); *A61K 47/48215* (2013.01); *A61K 47/48861* (2013.01); *A61K 47/48884* (2013.01); *A61K 49/1842* (2013.01); *Y10T 428/2982* (2015.01)

(58) Field of Classification Search
None
See application file for complete search history.

(56) References Cited

U.S. PATENT DOCUMENTS

| | | | | |
|---|---|---|---|---|
| 5,492,814 | A * | 2/1996 | Weissleder ................. | 435/7.25 |
| 6,423,296 | B1 | 7/2002 | Gunther et al. | |
| 7,951,453 | B2 | 5/2011 | Dubertret et al. | |
| 2009/0111919 | A1* | 4/2009 | Lortz et al. ................... | 524/131 |
| 2009/0280063 | A1 | 11/2009 | Kulkarni et al. | |
| 2010/0111859 | A1 | 5/2010 | Axelsson et al. | |
| 2010/0111876 | A1 | 5/2010 | Corot | |
| 2010/0166664 | A1 | 7/2010 | Butts et al. | |
| 2010/0209354 | A1 | 8/2010 | Horcajada-Cortes et al. | |
| 2010/0215586 | A1 | 8/2010 | Port et al. | |
| 2010/0255103 | A1 | 10/2010 | Liong et al. | |
| 2010/0278748 | A1 | 11/2010 | Bonitatibus, Jr. et al. | |
| 2011/0104072 | A1* | 5/2011 | Bales et al. ................. | 424/9.32 |

FOREIGN PATENT DOCUMENTS

| | | |
|---|---|---|
| WO | 9725073 A2 | 7/1997 |
| WO | WO9832466 A1 * | 6/1998 |
| WO | 2011051422 A2 | 5/2011 |
| WO | 2012080290 A1 | 6/2012 |

OTHER PUBLICATIONS

Qi., L., et al., "Redispersible Hybrid Nanopowders: Cerium Oxide Nanoparticle Complexes with Phosphonated-PEG Oligomers", 2008, ACS Nano, pp. 879-888.*
Miles, W.C., et. al., "Design of Stable Polyether_Magnetite Complexes in Aqueous Media: Effects of the Anchor Group, Molecular Weight, and Chain Density" 2011, Langmuir, pp. 5456-5463.*
Larsen, E.K.U., et al., "Accumulation of magnetic iron oxide nanoparticles coated with variably sized polyethylene glycol in murine tumors", 2012, Nanoscale, pp. 2352-2361.*
Yamaoka, T., et al., "Distribution and Tissue Uptake of Poly(ethylene glycol) with Different Molecular Weights after Intravenous Administration to Mice", 1993, Pharmaceutical Sciences, pp. 601-606.*
Mosqueira, V.C.F., et al., "Biodistribution of Long-Circulating PEG-Grafted Nanocapsules in Mice Effects of PEG Chain Length and Density", Pharmaceutical Research, 2001, pp. 1411-1419.*
Search Report and Written Opinion from corresponding PCT Application No. PCT/EP2013/054016 dated Jun. 24, 2013.
Unofficial translation of Chinese Office Action issued in connection with corresponding Chinese Patent Application 201380011948.0 dated Oct. 26, 2015.
Unofficial translation of Chinese Office ActionSearch Report issued in corresponding connection with Chinese Patent Application 201380011948.0 dated Oct. 18, 2015.
Haiyan, Xu "Nanometer biological medicine carrier", Science Press, Feb. 2012 pp. 215-217 and 224. (unofficial translation).
Lodhia et al., "Development and use of iron oxide nanoparticles (Part 1): Synthesis of iron oxide nanoparticles for MRI", Biomedical Imaging and Interventional Journal, vol. 6, No. 2, 2010.

* cited by examiner

*Primary Examiner* — Michael G Hartley
*Assistant Examiner* — Lance Rider
(74) *Attorney, Agent, or Firm* — Paul J. DiConza (57) ABSTRACT

The present application discloses nanoparticles, particularly nanoparticles of superparamagnetic iron oxide, which find utility in iron therapy and diagnostic imaging such as magnetic resonance (MR). The disclosed nanoparticles have been treated with an α-hydroxyphosphonic acid conjugate containing polyethylene glycol as a hydrophilic moiety to render the nanoparticles sufficiently hydrophilic to find utility in diagnostic imaging. Among the modified hydrophilic nanoparticles disclosed are those in which the hydrophilic moieties of the modifying conjugate are polyethylene oxide-based polymers and have a molecular weight greater than 5,000 dalton and less than or equal to about 30,000 daltons. Surprisingly, these nanoparticles have a more rapid and complete processing in liver of retained nanoparticles when compared to similar nanoparticles in which the PEG-based hydrophilic moiety has a molecular weight less than 5,000.

42 Claims, 2 Drawing Sheets

SUPERPARAMAGNETIC NANOPARTICLES WITH PEG SUBSTITUTED α-HYDROXY PHOSPHONATE SHELLS

BACKGROUND

The invention relates generally to nanoparticles, particularly those based on transition metal oxides, which have been treated with an α-hydroxy phosphonic acid derivative to render them sufficiently hydrophilic to form stable aqueous suspensions. The modified nanoparticles are useful in applications requiring hydrophilicity such as for use as therapeutic agents and as contrast agents in diagnostic imaging, for example, by magnetic resonance imaging (MRI).

In some applications, for example, when used as contrast agents or therapeutic agents, it is also desirable that the nanoparticles have a well defined reproducible structure and be amenable to safety testing. Accordingly, there has been a need for hydrophilic nanoparticles that do not suffer a degradation of their hydrophilicity as a result of purification and display suspension stability in aqueous mediums containing electrolytes. For instance, in the preparation of contrast agents for in vivo use in human subjects the candidate nanoparticles would typically be subjected to purification and be expected to show suspension stability in isotonic aqueous media, i.e. media containing about 150 mM NaCl. Efforts to enhance nanoparticle hydrophilicity and stability in saline by coating transition metal oxide particles with α-hydroxyphosphonic acid-PEG conjugates having molecular weights up to about 5,000 daltons have had some success.

To date, little if any information has been available regarding in vivo behavior of these modified particles. In particular, parameters related to residence time in the body are important to consider when nanoparticles are developed for use in diagnostic imaging, or if use as a therapeutic agent is contemplated. Residual MR signal from unprocessed iron oxide nanoparticles retains a strong MR signal, which is undesirable when repeat dosing of the agent is required in the clinical workflow. In that regard, the modified nanoparticles disclosed herein exhibit improved processing, such as in the liver, despite enhanced stability.

BRIEF DESCRIPTION

It had been previously observed that an increase in the polyethylene glycol (PEG) molecular weight of an α-hydroxyphosphonic acid-based coating material shifts the resulting superparamagnetic iron oxide (SPIOs) nanoparticle towards a more stable profile, and a longer blood half-life. What was unexpected was the subsequent observation that despite increased stability in blood and serum, SPIOs with α-hydroxyphosphonic acid-PEG conjugates where the PEG is greater than 5000 molecular weight, exhibit more rapid liver processing of retained dose. Accordingly, the present disclosure relates to SPIOs coated with an α-hydroxyphosphonic acid conjugate that includes a PEG with a molecular weight greater than about 5,000 daltons less and than or equal to about 30,000 daltons. In one embodiment, for example, conjugates with PEG of molecular weight greater than 5,000 daltons have surprisingly more rapid and complete liver processing relative to the same coating material with PEGs with molecular weights lower than 5,000 daltons.

In one aspect, therefore, the invention relates to a nanoparticle composition comprising nanoparticles having an iron oxide core to which is adhered an α-hydroxyphosphonate moiety, wherein the α-hydroxy phosphonate moiety has the structure of formula I:

Formula I wherein S is a spacer, L is a linkage between S and R, R is a poly(ethylene glycol), and Z is an alkoxy or hydroxy endcap at the ω end of the PEG chain wherein, said PEG has a molecular weight greater than about 5000 daltons and less than or equal to about 30,000 daltons and o=0 or 1.

In some embodiments, S is a direct bond, an unsubstituted or substituted aliphatic or cycloaliphatic group, a heteroaliphatic group and in some cases is a straight chain alkyl group of 1 to 10 carbon atoms in length and L is a direct bond, carbonyl group, ether group, ester group, secondary or tertiary amine, quaternary amine group, amide group, carbamate group or urea group.

It is of particular interest that the conjugate not include groups or moieties which could have undesirable reactions with human tissue. Thus, it is convenient that the conjugate display a zeta potential between about −40 mV and 40 mV, preferably between about −15 mV and 15 mV when adhered to a nanoparticle with it being especially interesting that it display an essentially neutral zeta potential when so adhered.

It is also convenient for conjugates used to treat nanoparticles to be used in vivo with human subjects that the linkage between the α-hydroxyphosphonic acid and the PEG be a hydrocarbon, i.e. in Structure I, S is a single bond.

The disclosure further relates to a method of diagnostic imaging using PEG-substituted alpha-hydroxy phosphonate coated nanoparticles comprising:

subjecting to imaging an individual to whom a nanoparticle composition has been administered, the nanoparticle composition comprising iron oxide nanoparticles to which is adhered an α-hydroxyphosphonate moiety, wherein the α-hydroxy phosphonate moiety has the structure of formula I:

Formula I wherein S is a spacer, L is a linkage between S and R, R is a poly(ethylene glycol), and Z is an alkoxy or hydroxy cap at the ω end of the PEG chain and o=0 or 1, and wherein said PEG has a molecular weight greater than about 5000 daltons and less than or equal to about 30,000 daltons.

In a yet another aspect, the invention relates to a method of treating an iron deficiency using PEG-substituted alpha-hydroxy phosphonate coated nanoparticles comprising:

administering to an individual a nanoparticle composition comprising nanoparticles having an iron oxide core to which is adhered an α-hydroxyphosphonate moiety, wherein the α-hydroxy phosphonate moiety has the structure of formula I:

Formula I wherein S is a spacer, L is a linkage between S and R, R is a poly(ethylene glycol), and Z is an alkoxy or hydroxy cap at the ω end of the PEG chain wherein said PEG has a molecular weight greater than about 5000 daltons and less than or equal to about 30,000 daltons, and o=0 or 1.

The α-hydroxyphosphonic acid-PEG conjugate is preferably sufficiently hydrophilic that when it is used to treat nanoparticles at a ratio of about 0.04 to about 2.0 conjugates per Fe atom it will render the nanoparticles capable of forming stable colloidal suspensions in aqueous media with a $D_H$ determined by DLS of about 15 to 100 nm, in some embodiments between about 15 an 50 nm and in still other embodiments, between about 20 and about 30 nm. It is particularly convenient that it render so treated nanoparticles hydrophilic enough to display a value of less than one for the log of the distribution coefficient between equal volumes of n-octanol and 0.1 M pH 7.0 3-(N-morpholino) propanesulfonic acid (MOPS) buffer.

The nanoparticle cores to be modified by addition of the α-hydroxyphosphonic acid-PEG conjugate are preferably those based on transition metals and transition metal compounds such as oxides, carbides, sulfides, nitrides, phosphides, borides, halides, selenides, tellurides and combinations thereof. Oxides are of particular interest. Transition metal compounds are useful for preparing contrast agents for magnetic resonance (MR) imaging. The transition metals of the third period of the Periodic Table of Elements are useful for forming compounds that display paramagnetism and conveniently superparamagnetism and therefore are useful as MRI contrast agents. Especially convenient are superparamagnetic nanoparticles based upon iron oxide. These are commonly referred to as superparamagnetic iron oxide (SPIO) particles and methods for the fabrication of SPIO nanoparticles is known to those of skill in the art (for example, see Lodhia et al. *Development and use of iron oxide nanoparticles (Part I): Synthesis of iron oxide nanoparticles for MRI.* Biomedical Imaging and Intervention Journal, 6(2):e12, 2010).

The hydrophilically modified nanoparticles typically have a $D_H$ as determined by DLS of about 15 nm to 100 nm and in some embodiments between 15 and 50 nm, and in still other embodiments, between about 20 nm and about 30 nm. If the hydrophilically modified nanoparticles are destined for in vivo use in human subjects as, for instance, MRI contrast agents, a particularly convenient $D_H$ is about 30 nm or less.

In one embodiment, the hydrophilically modified nanoparticles are prepared by reacting them with the conjugate. One approach is to form a colloidal suspension of the nanoparticles in an organic solvent such as benzyl alcohol (BnOH) and then mix it with an organic solution of the conjugate in the same or a different organic solution. The mixture may then be held for an elevated temperature for an extended period until the reaction is essentially complete. Typically temperatures of 50° C. or more for 16 hours or more are convenient.

Stable monodisperse aqueous colloidal suspensions of the hydrophilically modified nanoparticles are readily obtained. Such suspensions should preferably be stable against filtration such as tangential flow filtration against a 30 kDa cut off and the addition of electrolytes such as the addition of NaCl to render the aqueous medium isotonic, i.e. about 150 mM of NaCl. Preferably the suspensions are stable for storage periods of one week or greater and more preferably are stable against not only sedimentation but also against growth of the $D_H$ as determined by DLS of the suspended nanoparticles. If the suspensions are intended for in vivo use in human subjects, it is convenient to render them isotonic by the addition of NaCl, dextrose, or with other tonicity modifiers known in the art or combinations thereof.

The hydrophilically modified nanoparticles may be conveniently used as therapeutic agents or as contrast agents in diagnostic imaging. Common types of diagnostic imaging include magnetic resonance (MR) imaging. Therapeutic administration of the hydrophilically modified nanoparticles as an iron supplement is also envisaged, for example, for the treatment of iron deficiency.

In either therapy or imaging, it is convenient to use hydrophilically modified nanoparticles which have a zeta potential between about –15 mV and 15 mV. A convenient approach to the administration of the hydrophilically modified nanoparticles to human subjects is to administer the nanoparticles intraveneously, preferably as a stable isotonic aqueous suspension. If the use is for MR imaging, the nanoparticles should comprise a paramagnetic, preferably superparamagnetic species, and most preferably they should be iron oxide based such as magnetite or maghemite.

DRAWINGS

These and other features, aspects, and advantages of the present invention will become better understood when the following detailed description is read with reference to the accompanying drawings.

DETAILED DESCRIPTION

In the description that follows, unless otherwise stated, the interpretation of terms used is intended to be consistent with the normal meaning of those term(s).

The conjugates of the present invention may have a wide variety of linkages. A key feature is that the conjugate has the three hydroxyl groups of the α-hydroxyphosphonic acid that are chemically and sterically accessible. While the structure has chiral centers, it is expected that all of the individual enantiomers and possible racemic mixtures would be suitable to impart hydrophilicity to water insoluble nanoparticles.

These conjugates may have any of the commonly known chemical linkages between the α-hydroxyphosphonic acid structure and the PEG including those based upon carbon, nitrogen, oxygen and sulfur. Groups of particular interest are hydrocarbon, carbonyl, ester, ether, secondary or tertiary amine, quaternary amine, urea, carbamate and amide. The intended end use of the nanoparticles to be treated with the conjugate may impact the choice of linkage group. For instance if the nanoparticles are to be used in vivo, particularly in human subjects, The most interesting linkage group from the standpoint of inertness is a hydrocarbon.

The conjugates presently disclosed are based on ethylene oxide with the poly(ethylene oxides/glycols), having an average molecular weight greater than about 5,000 daltons and less than or equal to about 30,000 daltons.

When reference is made herein to the molecular weight of poly(ethylene glycol) (PEG), the disclosed value represents an average molecular weight for the compound; a preparation of that compound may include species that vary in molecular weight from the average anywhere from 10-28%. For example, as indicated by the manufacturer, a preparation of PEG 3350 has an average molecular weight of 3350 daltons with molecular species in the preparation having molecular weights between 3000 and 3750. Spectral analysis of the PEG 5000 material used showed a size range from about 4,000 to 6,400 daltons with the average being around 5,000 daltons.

In some embodiments, nanoparticles are treated with a PEG-α-hydroxyphosphonic acid conjugate having the structure of Formula II:

Formula II where n=1 or 2 and p~114-681.

In some embodiments, the conjugate is made by first preparing the α-hydroxyphosphonic acid in accordance with the following synthetic scheme in which R is PEG:

Scheme 1

In other embodiments, the conjugate is made in accordance with the following synthetic scheme:

The conjugate is preferably sufficiently hydrophilic that it can render nanoparticles able to form stable aqueous suspensions when it is reacted with the nanoparticles at a ratio of about 0.04-2.0 equivalents of conjugate per metal basis of the nanoparticle. The nanoparticle will typically be based on a transition metal compound such as an oxide or a transition metal itself. It is convenient to specify the reaction ratio using the moles of elemental metal as this can be readily obtained from an elemental analysis of the starting suspension of nanoparticles in organic solvent. From a knowledge of the chemical make up of the nanoparticles and their average size before treatment, a rough calculation can be made of the amount of conjugate per nanoparticle. It is particularly convenient that the conjugate be hydrophilic enough to provide coated nanoparticles of iron oxide between 15 nm and 100 nm, in some embodiments between 15 nm and 50 nm and in still other embodiments between about 20 and about 30 nm, yielding particles with sufficient hydrophilicity to display a value of less than one for the log of the distribution coefficient between equal volumes of n-octanol and 0.1 M pH 7.0 MOPS buffer.

It is of particular interest that the modified hydrophilic nanoparticles with an adhered alpha-hydroxyphosphonic acid conjugate be sufficiently hydrophilic to form a stable aqueous colloidal suspension that exhibits no substantial change in hydrodynamic diameter ($D_H$) as determined by dynamic light scattering (DLS) in 150 mM NaCl water after tangential flow filtration. The nanoparticles that are to be treated with the conjugate can be of any water insoluble material that can be formed into particles of 100 nm or less to which the α-hydroxy phosphonic acid portion of the conjugate will adhere. It is of interest to use nanoparticles that have utility as contrast agents in magnetic resonance imaging. Additionally, the use of the nanoparticles of the disclosure in a therapeutic manner is also contemplated. However, nanoparticles for other end uses such as infusion of cell cultures for transfection of genes are also of interest.

For use as MRI contrast agents the basis of the nanoparticles should be a metal or its compounds that are paramagnetic, with those that are superparamagnetic being of particular interest. These metals are conveniently drawn from the transition metals of Period III of the Periodic Table of Elements beginning with manganese and ending with zinc. For use in therapy as well as in imaging, a particularly interesting group of materials are those based upon iron oxide. Especially convenient materials are those known as SPIO's. These materials have the general formula $[Fe_2^+O_3]_x$ $[Fe_2^+O_3(M^{2+}O)]_{1-x}$ where $1 \geq x \geq 0$. $M^{2+}$ may be a divalent metal ion such as iron, manganese, nickel, cobalt, magnesium, copper, zinc or a combination thereof. When the metal ion ($M^{2+}$) is ferrous ion ($Fe^{2+}$) and x=0, the material is magnetite ($Fe_3O_4$), and when x=1, the material is maghemite ($\gamma\text{-}Fe_2O_3$).

In general, superparamagnetism occurs when crystal-containing regions of unpaired spins are sufficiently large that they can be regarded as thermodynamically independent, single domain particles called magnetic domains. These magnetic domains display a net magnetic dipole that is larger than the sum of its individual unpaired electrons. In the absence of an applied magnetic field, all the magnetic domains are randomly oriented with no net magnetization. Application of an external magnetic field causes the dipole moments of all magnetic domains to reorient resulting in a net magnetic moment. In some embodiments, these materials demonstrate a spinel crystalline structure as shown by transmission electron microscope (TEM) analysis.

The modified hydrophilic nanoparticles to which the α-hydroxyphosphonic acids have been adhered may be used as therapeutic agents or as contrast agents in diagnostic imaging. In an imaging application, the modified nanoparticles are administered to a subject, in some embodiments a mammalian subject, and then the subject is subjected to imaging. In a therapeutic application, the modified nanoparticles are administered to a subject, for example, to address an iron deficiency.

When used in diagnostic imaging, particularly of mammalian subjects and more particularly of human subjects, the modified hydrophilic nanoparticles to which the α-hydroxyphosphonic acids have been adhered are typically taken up in a pharmaceutically acceptable carrier which may or may not comprise one or more excipients. If the administration is to be by injection, particularly parenteral injection, the carrier is typically an aqueous medium that has been rendered isotonic by the addition of about 150 mM of NaCl, 5% dextrose or combinations thereof. It typically also has the physiological pH of between about 7.3 and 7.4. The administration may be intramuscular (IM), subcutaneous (SQ) or most commonly intravenous (IV). However, the administration may also be via implantation of a depot that then slowly releases the nanoparticles to the subject's blood or tissue.

Alternatively, the administration may be by ingestion for imaging of the GI tract or for oral delivery of a therapeutic iron dose or, by inhalation for imaging of the lungs and airways.

The administration to human subjects, particularly IV administration, requires that the modified hydrophilic nanoparticles to which the α-hydroxyphosphonic acids have been adhered be non-toxic in the amounts used and free of any infective agents such as bacteria and viruses and also free of any pyrogens. Thus, these nanoparticles should be stable to the necessary purification procedures and not suffer a degradation in their hydrophilicity.

These nanoparticles may be delivered to the site of administration as a stable aqueous colloidal suspension with the proper osmolality and pH, as a concentrated aqueous colloidal suspension suitable for dilution and adjustment or as a powder, such as obtained by lyophilization, suitable for reconstitution.

The present disclosure, therefore, further relates to methods for imaging a subject using the nanoparticles disclosed herein. Such method comprises the step of subjecting a subject to whom a nanoparticle composition has been administered to imaging, for example by magnetic resonance, wherein said composition administered to the subject comprises nanoparticles to which is adhered a α-hydroxyphosphonate-PEG conjugate, said PEG having a molecular weight greater than about 5,000 daltons, and less than or equal to about 30,000 daltons.

Previous efforts to generate PEG-α-hydroxyphosphonic acid modified superparamagnetic iron oxide particles (SPIOs) resulted in SPIOs with improved hydrophilicity and stability. In imaging experiments, however, a "dual phase" biexponential decay in MR signal attributable to the persistence of nanoparticles in the liver was observed.

Figure 1:
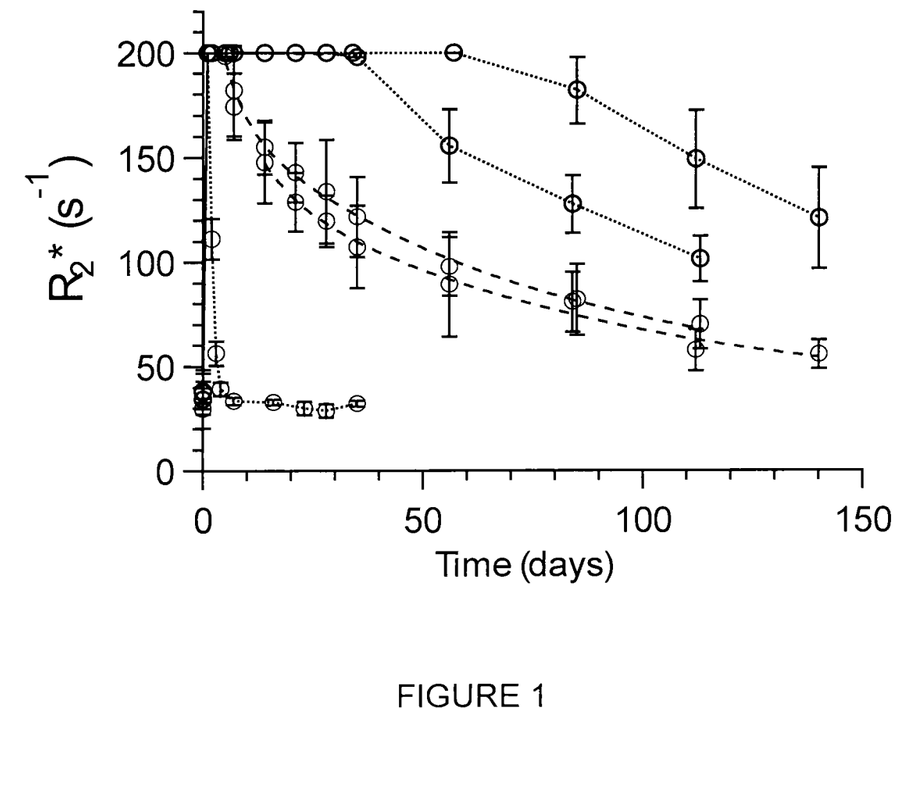
FIG. 1 is a graph showing the results of a liver clearance study comparing hydrophilically modified nanoparticles with PEGs of various average molecular weights, including 350, 440, 750, 2,000, and 5,000 daltons.
Figure 2:
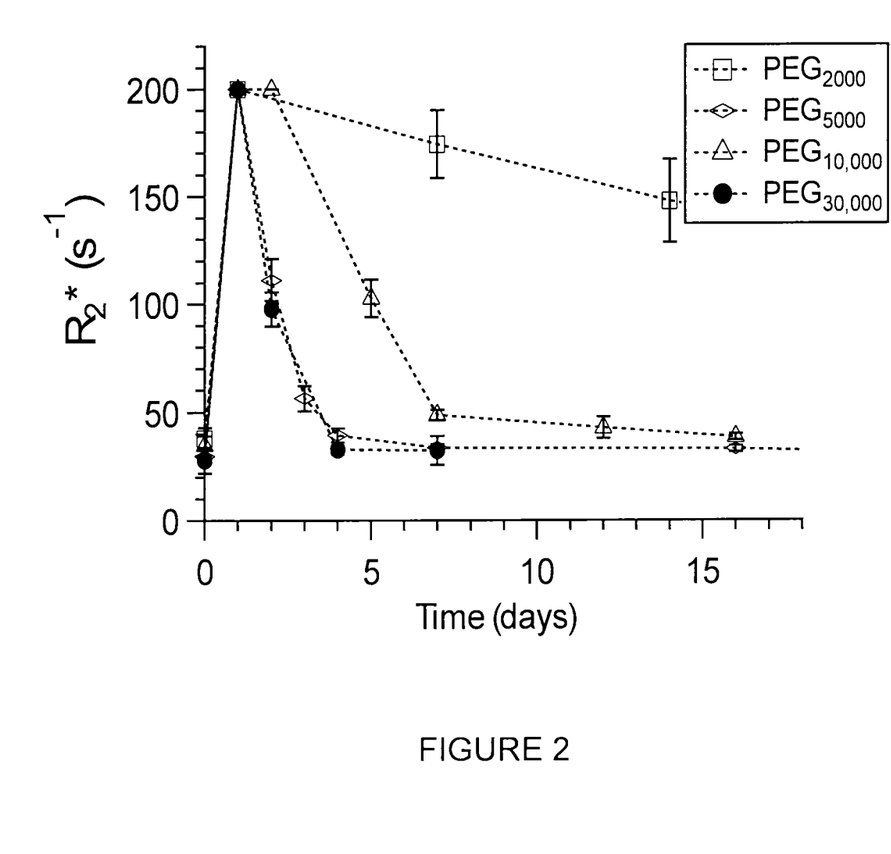
FIG. 2 is a graph showing the results of a liver clearance study comparing hydrophilically modified nanoparticles with PEGs of average molecular weight 2,000, 5000, 10,000 and 30,000 daltons.

Closer evaluation of the PEG molecular weight of the hydrophilic conjugate used to coat the nanoparticles showed that liver processing characteristics appeared to track with PEG polymer size. As shown in FIGS. 1 and 2, those nanoparticles modified with a PEG-α-hydroxyphosphonic acid in which the molecular weight of the PEG is greater than about 5,000 daltons (PEG5000) had a distinctly more rapid and complete liver processing profile over those with PEG of molecular weight of about 2000 daltons (PEG2000).

No significant difference in liver uptake of iron between PEG2000- and PEG5000-based SPIO nanoparticles was observed at 24 hours following injection, as measured via inductively coupled plasma mass spectroscopy using isotopically enriched iron oxide nanoparticles (data not shown). Similarly, no significant difference was observed in quantities of exogenous or endogenous iron in liver up to at least 84 days following injection when measured by inductively coupled plasma mass spectroscopy (data not shown). However, despite these similar tissue iron levels for PEG2000- and PEG5000-based SPIO nanoparticles, a difference in the profile of processing of the iron oxide cores in the liver was apparent by MR imaging. The PEG5000-based SPIO nanoparticles show little or none of the slower, biexponential degradation profile assessed by MR imaging that was observed for SPIO nanoparticles comprising conjugates having PEG with molecular weight of 2000 or less daltons.

The written description uses the following examples to illustrate the disclosure, including the best mode, and also to enable any person skilled in the art to practice the disclosure. The patentable scope of the disclosure is defined by the claims, and may include other examples that occur to those skilled in the art.

EXAMPLES

Example 1

Synthesis of a PEG-350 Conjugate

Synthesis of PEG-350 mono(methyl ether) acetaldehyde

To a solution containing PEG-350 mono(methyl ether) (3.438 g, 9.82 mmol) dissolved in $CH_2Cl_2$ (98 mL) was added Dess-Martin Periodinane (5.00 g, 11.79 mmol) and the resulting solution was stirred at rt for 20 h. During the reaction a fine, white precipitate was formed and was removed at the end of the reaction via filtration through a celite pad. The solvent was removed from the filtrate in vacuo to leave a white solid suspended in a yellow oil. The solid was triturated with diethyl ether, and the solid was removed by filtration through a celite pad. Removal of the solvent from the filtrate in vacuo left the product PEG-350 mono(methyl ether) acetaldehyde (3.42 g, 100%) as a yellow oil. $^1$H NMR (CDCl$_3$) δ 9.73 (t, J=4 Hz, 1H), 4.16 (d, J=4 Hz, 2H), 3.65 (m, 24H), 3.38 (s, 3H) ppm. IR (neat) 2873, 1732, 1455, 1350, 1109, 1040, 948, 851, 749 cm$^{-1}$.

Synthesis of diethyl α-hydroxy PEG-350 mono(methyl ether) phosphonate

To a solution containing PEG-350 mono(methyl ether) acetaldehyde (3.71 g, 10.7 mmol) dissolved in tetrahydrofuran (53 mL) was added diethyl phosphite (1.77 g, 12.8 mmol). The solution was cooled to 0° C., and 1,8-diazabicyclo[5.4.0]undec-7-ene (1.94 g, 12.8 mmol). After stirring at 0° C. for 10 min, the rxn was warmed to rt and stirred for an additional 24 h. The solvent was removed in vacuo to leave a dark yellow oil which was purified via column chromatography (100% CH$_2$Cl$_2$ to 15% MeOH/85% CH$_2$Cl$_2$) to give 3.30 g (64%) of the desired diethyl α-hydroxy PEG-350 mono(methyl ether) phosphonate product as a yellow oil. $^1$H NMR (CDCl$_3$) δ 4.19 (m, 6H), 3.65 (m, 24H), 3.38 (s, 3H), 1.34 (m, 6H) ppm. $^{31}$P NMR (CDCl$_3$) δ 23.1 ppm. IR (neat) 3343, 2872, 1725, 1453, 1248, 1105, 965, 850, 791 cm$^{-1}$.

Synthesis of α-hydroxy PEG-350 mono(methyl ether) phosphonic acid

To a solution containing diethyl α-hydroxy PEG-350 mono(methyl ether) phosphonate (3.61 g, 7.43 mmol) dissolved in methylene chloride (74 mL) was added trimethylsilyl bromide (3.41 g, 22.3 mmol) and the resulting solution was stirred at rt for 2 h. The solvent was removed in vacuo to leave a brown oil. The resulting oil was dissolved in acetone (74 mL) and water (0.5 mL) and the resulting solution was stirred at rt for 1.5 h. The solvent was then removed in vacuo to leave the desired α-hydroxy PEG-350 mono(methyl ether) phosphonic acid product (2.66 g, 84%) as a golden oil. $^1$H NMR (CDCl$_3$) δ 3.65 (m, 24H), 3.38 (s, 3H). $^{31}$P NMR (CDCl$_3$) δ 24.0 ppm. IR (neat) 3460, 2870, 1727, 1456, 1351, 945, 849 cm$^{-1}$.

Example 2

Synthesis of a PEG-1900 Conjugate

Synthesis of mPEG2k-epoxide

A 2 L jacketed reaction vessel was purged with nitrogen and charged with epichlorohydrin (222.9 mL, 2.843 mol) followed by H$_2$O (11.37 mL, 0.631 mol). After stirring at rt for 10 min, NaOH (113.7 g, 2.843 mol) was added and the resulting reaction slurry was heated to 72° C. PEG$_{1900}$ mono(methyl ether) was added to the reaction and the resulting melt was stirred at 72° C. for 3 h. The reaction was then cooled to 35° C. and H$_2$O (750 mL) was added. Once the reaction solution reached rt, the aqueous reaction solution was extracted with CH$_2$Cl$_2$ (2×750 mL). The solvent was then removed from the combined organic extracts in vacuo to give a tan/brown solid. The solid was dissolved in CH$_2$Cl$_2$ (750 mL) and the resulting cloudy solution was passed through a celite pad. The solvent was removed from the resulting clear orange filtrate in vacuo to leave a waxy, tan solid. The recovered solid was recrystallized 2× from 2:1 THF/hexanes (1.3 mL THF/g crude) to give 439.7 g (85%) of the desired product as an off white solid: $^1$H NMR (CDCl$_3$) δ 3.76 (m, 2H), 3.60 (m, 186H), 3.39 (m, 2H), 3.33 (s, 3H), 3.12 (m, 1H), 2.75 (m, 1H), 2.57 (m, 1H). $^{13}$C NMR (CDCl$_3$) δ 72.12, 72.06, 70.87, 70.70, 59.18, 50.95, 44.39.

Synthesis of mPEG2k-diol mPEG2k-epoxide (125.0 g, 63.9 mmol) was dissolved in 0.5 M H$_2$SO$_4$ (500 mL) and the resulting solution was stirred at rt for 1 h. The reaction solution was then with CH$_2$Cl$_2$ (2×500 mL). The solvent was removed from the combined organic layers in vacuo to give a waxy, tan solid. The recovered solid was recrystallized from 2:1 THF/hexanes (0.83 mL THF/g crude) to give 115.8 g (93%) of the desired product as an off white powder: $^1$H NMR (CDCl$_3$) δ 3.71 (m, 2H), 3.53 (m, 182H), 3.35 (m, 1H), 3.26 (s, 3H). $^{13}$C NMR (CDCl$_3$) δ 73.00, 72.05, 70.85, 64.03, 59.16.

Synthesis of mPEG2k-aldehyde mPEG2k-diol (5.0 g, 2.53 mmol) was dissolved in H$_2$O (14.7 mL) and the reaction solution was cooled to 6° C. A solution containing NaIO$_4$ (0.650 g, 3.04 mmol) dissolved in H₂O (4.42 mL) was added in 3 equal aliquots over a period of 10 min. The resulting solution was stirred at 6° C. for 1 h. 1,2-Propanediol (0.100 mL, 0.136 mmol) was added and the reaction was stirred at 6° C. for an additional 15 min. The reaction was then warmed to rt and the aqueous reaction mixture was extracted with CH₂Cl₂ (3×20 mL). The combined organic layers were washed with brine (15 mL) and the solvent was removed in vacuo to leave 4.59 g (93%) of the desired product as an off white waxy solid. $^1$H NMR (CDCl₃) δ 9.67 (m, 1H), 4.11 (m, 2H), 3.76 (m, 1H), 3.58 (m, 170H), 3.40 (m, 1H), 3.32 (s, 3H).

Synthesis of dibenzyl-αHmPP5k mPEG2k-aldehyde (79.00 g, 40.7 mmol) was dissolved in CH₂Cl₂ (136.5 mL). Dibenzyl phosphite (8.99 mL, 40.7 mmol) was added followed by triethylamine (5.65 mL, 40.68 mmol). After stirring at rt for 20 h, the solvent was removed from the reaction mixture in vacuo to leave a waxy, yellow solid. The recovered solid was recrystallized from 2:1 THF/hexanes (2 mL THF/g crude) to give 81.0 g (90%) of the desired product as an off white powder. $^1$H NMR (CDCl₃) δ 7.30 (m, 10H), 5.06 (m, 4H), 4.16 (m, 1H), 3.78 (m, 2H), 3.59 (m, 163H), 3.42 (m, 1H), 3.34 (s, 3H). $^{13}$C NMR (CDCl₃) δ 128.78, 128.63, 128.47, 128.10, 128.03, 72.01, 71.32, 70.84, 70.65, 68.17, 68.10, 67.86, 67.34. $^{31}$P NMR (CDCl₃) δ 23.97.

Synthesis of αHmPP2k

Dibenzyl-αHmPP5k (80.0 g, 36.3 mmol) was dissolved in 95% ethanol (471.4 mL) and 10% Pd on carbon (2.87 g, 2.7 mmol Pd) was slowly added with stirring. The reaction was placed under an atmosphere of H₂ and stirred until H₂ uptake was complete (93 h). The Pd on carbon was removed via filtration through a celite pad and the solvent was removed from the filtrate in vacuo to leave a white, waxy solid. The recovered solid was recrystallized from 2:1 THF/hexanes (1.3 mL THF/g crude) to give 79.2 g (~100%) of the desired product as a white powder. $^1$H NMR (CDCl₃) δ 3.65 (m, 2H), 3.47 (m, 165H), 3.29 (m, 2H), 3.20 (s, 3H). $^{13}$C NMR (CDCl₃) δ 72.37, 71.59, 70.62, 70.22, 61.18, 58.68. $^{31}$P NMR (CDCl₃) δ 22.85.

Example 3

Synthesis of αPEG-5000 Conjugate

Synthesis of mPEG5k-epoxide

Water (4.32 mL) was suspended in epichlorohydrin (84.68 mL, 1.080 mol) and NaOH (43.20 g, 1.080 mmol) was added followed by triethylammonium hydrochloride (1.18 g, 0.009 mol). The solution was stirred and heated to 70° C. during which time PEG5000 mono(methyl ether) (500 g, 0.100 mol) was added in portions as the temperature rose. The resulting suspension was stirred at temp for 4 h and then cooled to rt. Water (500 mL) was added and the product was extracted with CH₂Cl₂ (2×1000 mL). The CH₂Cl₂ was removed in vacuo (not to dryness—but only to a thick oil) and the resulting oil was recrystallized from THF (400 mL)/hexanes (200 mL) (add THF, heat and then add hexanes, swirl until cloudiness clears ~30 s) to give 499.93 g (99% of theoretical mass) of the desired product as an off white solid: $^1$H NMR (CDCl₃) δ 3.81 (m, 2H), 3.64 (m, 422H), 3.46 (m, 2H), 3.38 (s, 3H), 3.17 (m, 1H), 2.79 (m, 1H), 2.61 (m, 1H). $^{13}$C NMR (CDCl₃) δ 71.97, 71.89, 70.53, 59.00, 50.76, 44.22.

Synthesis of mPEG5k-diol mPEG5k-epoxide (499.93 g, 98.88 mmol) was dissolved in 0.5 M H₂SO₄ (2000 mL) and stirred at rt for 1.5 h (~30 min to fully dissolve material and the 1 additional hour reaction). The reaction was then extracted with CH₂Cl₂ (2×1000 mL). The CH₂Cl₂ was removed in vacuo (not to dryness—but only to a thick oil) and the resulting oil was recrystallized from THF/hexanes (400 mL:200 mL) (add THF, heat and then add hexanes, swirl until cloudiness clears ~30 s) to give 411.88 g (82% of theoretical mass) of the desired product as an off white solid: $^1$H NMR (CDCl₃) δ 3.75 (m, 2H), 3.57 (m, 422H), 3.39 (m, 2H), 3.31 (s, 3H). $^{13}$C NMR (CDCl₃) δ 72.88, 71.91, 70.55, 63.93, 59.02.

Synthesis of mPEG5k-aldehyde mPEG5k-diol (208 g, 40.99 mmol) was dissolved in water (320 mL) and stirred at rt for ~45 min. To this cloudy solution was added a pre-dissolved solution of NaIO₄ (10.7 g, 50 mmol) in water (90 mL) was added in equal portions over ~30 min. The cloudiness cleared after ~1.5-2 h following the final oxidant addition. The reaction was then stirred for 16 h and quenched by the addition of propylene glycol (1.20 mL). The aqueous reaction mixture was then extracted with CH₂Cl₂ (1×1000 mL, 1×500 mL). The organic layers were combined, and the CH₂Cl₂ was removed in vacuo (not to dryness—but only to a thick oil). The resulting golden oil was recrystallized from THF/hexanes (400 mL:200 mL) (add THF, heat and then add hexanes, swirl until cloudiness clears ~30 s) to yield 183.77 g (89% of theoretical mass) of the desired product as a white solid: $^1$H NMR (CDCl₃) δ

9.66 (m, 1H), 4.10 (m, 2H), 3.75 (m, 2H), 3.58 (m, 422H), 3.39 (m, 2H), 3.31 (s, 3H). $^{13}$C NMR (CDCl$_3$) δ 200.94, 71.90, 71.18, 70.54, 59.01, 53.56.

Synthesis of dibenzyl-αHmPP5k mPEG5k-aldehyde (181.453 g, 35.97 mmol) was dissolved in CH$_2$Cl$_2$ (850 mL) and triethylamine (5.01 mL, 35.97 mmol) was added and allowed to stir for ~30 min. This was followed by a slow addition of dibenzyl phosphite (9.43 g, 35.97 mmol). After stirring at rt for 48 h, the solvent was removed in vacuo (not to dryness—but only to a thick oil) and the resulting oil was recrystallized from THF/hexanes (350 mL:175 mL) (add THF, heat and then add hexanes, swirl until cloudiness clears ~30 s) to give 175.59 g (92% of theoretical mass) of the desired product as a white solid: $^1$H NMR (CDCl$_3$) δ 7.34 (m, 10H), 5.10 (m, 4H), 3.79 (m, 1H), 3.75 (m, 2H), 3.64 (m, 460H), 3.53 (m, 4H), 3.37 (s, 3H). $^{13}$C NMR (CDCl$_3$) δ 136.40, 136.27, 128.74, 128.60, 128.43, 127.99, 71.98, 71.17, 70.61, 68.67, 68.13, 64.85, 67.59, 59.08. $^{31}$P NMR (CDCl$_3$) δ 23.92.

Synthesis of αHmPP5k

Dry dibenzyl-αHmPP5k (122.80 g, 23.15 mmol) was suspended in absolute ethanol (500 mL) and water (25 mL) and 10% Pd on carbon (4.0 g) was slowly added. The reaction was then stirred under an atmosphere of H2 (balloon pressure) until uptake was complete. The Pd on carbon was removed via filtration through a celite pad, and the solvent was removed from the filtrate in vacuo (not to dryness—but only to a thick oil). The resulting oil was recrystallized from THF/hexanes (300 mL:150 mL) to give 109.7 g (94% of theoretical mass) of the desired product as a white powder: $^1$H NMR (CDCl$_3$) δ 3.81 (m, 4H), 3.64 (m, 366H), 3.47 (m, 2H), 3.38 (s, 3H). $^{13}$C NMR (CDCl$_3$) δ 72.00, 71.04, 70.54, 59.11. $^{31}$P NMR (CDCl$_3$) δ 22.85.

Example 4

Synthesis of PEG-10,000 Conjugate

Synthesis of mPEG10k-diol

PEG$_{10000}$ mono(methyl ether) (20 g, 2 mmol) was heated to 80° C. during which time water (0.090 mL), epichlorohydrin (1.78 mL, 22.7 mmol), and NaOH (0.908 g, 22.7 mmol) was added followed by triethylammonium hydrochloride (0.025 g, 0.182 mmol). The resulting melt/suspension was stirred at temp for 18 h and then cooled to rt. 0.5 M H$_2$SO$_4$ (100 mL) was added and the reaction was stirred at rt for an additional 18 h. The product was extracted with CH$_2$Cl$_2$ (1×200 mL, 1×100 mL). The CH$_2$Cl$_2$ was removed in vacuo (not to dryness—but only to a thick oil) and the resulting oil was recrystallized from THF (150 mL)/hexanes (75 mL) (add THF, heat and then add hexanes, swirl until cloudiness clears ~30 sec) to yield 18.378 g (91% of theoretical mass) of the desired product as a white solid. This material was carried forward to the next step without further purification. $^1$H NMR δ (CDCl$_3$): 3.8 (8H, m), 3.5-3.75 (856H, bs), 3.44-3.48 (5H, m), 3.38 (3H, s).

Synthesis of mPEG10k-aldehyde mPEG10k-diol (17.805 g, 1.824 mmol) was dissolved in water (75 mL) and stirred at rt for ~30 min. To this cloudy solution was added a pre-dissolved solution of NaIO$_4$ (0.456 g, 2.22 mmol) in water (4.5 mL) was added in equal portions over ~30 min. The cloudiness clears after ~1.5 h following the final oxidant addition. The reaction was then stirred for 18 h and quenched by the addition of propylene glycol (0.054 mL). This reaction mixture was stirred for an additional 1 h. The aqueous reaction mixture was then extracted with CH$_2$Cl$_2$ (1×150 mL, 1×100 mL). Combine organics and the CH$_2$Cl$_2$ was removed in vacuo (not to dryness—but only to a thick oil) and the resulting yellow oil was recrystallized from THF/hexanes (200 mL: 100 mL) (add THF, heat and then add hexanes, swirl until cloudiness clears ~30 sec) to yield 13.182 g (72% of theoretical mass) of the desired product as a white solid. This material was carried forward to the next step without further purification. $^1$H NMR δ (CDCl$_3$): 9.74 (1H, s), 4.17 (2H, d), 3.82 (6H, m), 3.52-3.76 (880H, bs), 3.46-3.48 (5H, m), 3.38 (3H, s).

Synthesis of dibenzyl-αHmPP10k mPEG10k-aldehyde (18.475 g, 1.242 mmol) was dissolved in CH$_2$Cl$_2$ (50 mL) and triethyl amine (0.26 mL, 1.86 mmol) was added and allowed to stir for ~30 min. This was followed by a slow addition of dibenzyl phosphite (0.488 g, 1.86 mmol). After stirring at rt for 96 h, the solvent was removed in vacuo (not to dryness—but only to a thick oil) and the resulting oil was recrystallized from THF/hexanes (150 mL:75 mL) (add THF, heat and then add hexanes, swirl until cloudiness clears ~30 sec) to yield 12.53 g (98% of theoretical mass) of the desired product as a white solid. This material was carried forward to the next step without further purification. $^1$H NMR δ (CDCl$_3$): 7.36 (10H, m), 5.10 (4H, m), 4.2 (1H, M), 3.83 (9H, m), 3.54-3.74 (872H, bs), 3.46-3.48 (5H, m), 3.38 (3H, s).

Synthesis of aHmPP10k

Dibenzyl-aHmPP10k (11.81 g, 1.15 mmol) was suspended in absolute ethanol (100 mL) and heated at 40° C. until fully dissolved. 10% Pd on carbon (2.0 g) was slowly added. The reaction was then stirred under an atmosphere of H$_2$ (balloon pressure) at 40° C. until uptake was complete. The Pd on carbon was removed via filtration through a celite pad, and the solvent was removed from the filtrate in vacuo (not to dryness—but only to a thick oil). The resulting oil was recrystallized from THF/hexanes (150 mL:75 mL) to yield 11.27 g (98% of theoretical mass) of the desired product as a white powder. $^1$H NMR δ (CDCl$_3$): 3.95 (1H, m), 3.42-3.9 (900H, bs), 3.39 (3H, s).

Example 5

Synthesis of PEG-30,000 Conjugate

Synthesis of mPEG30k-diol

PEG$_{30000}$ mono(methyl ether) (30 g, 1 mmol) was heated to 85° C. during which time water (0.040 mL), epichlorohydrin (0.89 mL, 11.35 mmol), and NaOH (0.454 g, 11.35 mmol) was added followed by triethylammonium hydrochloride (0.013 g, 0.091 mmol). The resulting melt/suspension was stirred at temp for 10 min, at 95° C. for 30 min, 105° C. for 2.5 h, and then at 95° C. for an additional 1 h. The reaction was then cooled to rt. 0.5 M H$_2$SO$_4$ (100 mL) was added and the reaction was stirred at rt for an additional 18 h. The product was extracted with CH$_2$Cl$_2$ (2×150 mL). The CH$_2$Cl$_2$ was removed in vacuo (not to dryness—but only to a thick oil) and the resulting oil was recrystallized from THF (150 mL)/hexanes (75 mL) (add THF, heat and then add hexanes, swirl until cloudiness clears ~30 sec) to yield 17.91 g (60% of theoretical mass) of the desired product as a white solid. This material was carried forward to the next step without further purification.

Synthesis of mPEG30k-aldehyde mPEG30k-diol (17.0 g, 0.565 mmol) was dissolved in water (50 mL) and stirred at rt for ~30 min. To this cloudy solution was added a pre-dissolved solution of NaIO$_4$ (0.147 g, 0.69 mmol) in water (10 mL) was added as a single portion. The cloudiness clears after ~45 min following the oxidant addition. The reaction was then stirred for 18 h and quenched by the addition of propylene glycol (0.0165 mL). This reaction mixture was stirred for an additional 1 h. The aqueous reaction mixture was then extracted with CH$_2$Cl$_2$ (2×100 mL). Combine organics and the CH$_2$Cl$_2$ was removed in vacuo (not to dryness—but only to a thick oil) and the resulting yellow oil was recrystallized from THF/hexanes (150 mL:75 mL) (add THF, heat and then add hexanes, swirl until cloudiness clears ~30 sec) to yield 15.08 g (89% of theoretical mass) of the desired product as a white solid. This material was carried forward to the next step without further purification.

Synthesis of dibenzyl-αHmPP30k mPEG30k-aldehyde (14.27 g, 0.475 mmol) was dissolved in CH$_2$Cl$_2$ (50 mL) and triethyl amine (0.132 mL, 0.95 mmol) was added and allowed to stir for ~30 min. This was followed by a slow addition of dibenzyl phosphite (0.249 g, 0.95 mmol). After stirring at rt for 72 h, the solvent was removed in vacuo (not to dryness—but only to a thick oil) and the resulting oil was recrystallized from THF/hexanes (200 mL:100 mL) (add THF, heat and then add hexanes, swirl until cloudiness clears ~30 sec) to yield 14.03 g (97% of theoretical mass) of the desired product as a white solid. This material was carried forward to the next step without further purification.

Synthesis of αHmPP30k

Dibenzyl-αHmPP30k (10.6 g, 0.35 mmol) was suspended in absolute ethanol (100 mL) and heated at 40° C. until fully dissolved. 10% Pd on carbon (0.4 g) was slowly added. The reaction was then stirred under an atmosphere of H$_2$ (balloon pressure) at 40° C. until uptake was complete. The Pd on carbon was removed via filtration through a celite pad, and the solvent was removed from the filtrate in vacuo (not to dryness—but only to a thick oil) to yield 9.22 g (88% of theoretical mass) of the desired product as a white solid.

Example 6

Synthesis of Nanoparticle Composition (αHmPP5k SPIO)

9.177 g αHmPP5k ligand was weighed into a 1 L Erlenmeyer flask containing a magnetic stir bar. 8.955 ml of NaOH solution (0.2 M) was added along with 104 ml deionized water and absolute EtOH (200 mL). The flask was covered with a watch glass and stirred with magnetic stirring and gentle heating until a clear colorless solution was obtained. The above solution was added to 2 L jacketed reactor with mechanical stirrer, Teflon anchor agitator, thermocouple, nitrogen inlet and bubbler, and a reflux condenser. The flask was rinsed with absolute EtOH (2×25 mL), and the rinse was added to the reactor. The clear, colorless solution was stirred at 100 rpm. 330.6 ml of iron oxide nanoparticle core solution in benzyl alcohol (6.05 g Fe/ml) was added to the reaction mixture via a base washed, DI water rinsed, oven dried graduated cylinder through the powder funnel. The graduated cylinder was rinsed with absolute EtOH (2×25 mL) and the rinse was added to the reactor. A single phase, dark red-brown solution was observed. The stirring rate was increased to 200 rpm and the reactor was stoppered and heated under nitrogen with stirring for 18 h at 50° C. (internal temperature). After heating for 18 h, the reactor was cooled to 25° C. EtOAc (660 mL) and deionized water (320 mL) were added to the reactor and baffles were inserted for enhanced mixing. The reaction mixture was stirred at 500 rpm for 10 min. Stirring was stopped and the phases were allowed to separate. The cloudy mixture began to phase separate in <10 min and a clean phase split was observed after ~30 min. The lower aqueous phase (containing the SPIO particles), consisting of 247 grams of dark red-brown solution, was drained from the reactor into a 2 L 24/40 round bottomed flask. The solution was diluted with water to 800 mL (theory ~2.5 mg Fe/mL) and rotary evaporated briefly to remove any residual volatile organics. The solution was then sterile filtered (0.22 μm) and purified by tangential flow filtration (TFF) using a 50K PES Millipore 0.1 m² membrane. The product was washed with 24 L of deionized water over ~3 hr @ ~10 psi while maintaining a 2.5 L volume in the retentate reservoir. Permeate and retentate samples (~5 mL of each) were removed after each liter of permeate was collected. Once the washing was complete, the retentate was concentrated to ~120 grams (~16 mg Fe/mL). The final particles had a hydrodynamic diameter of 19.2 nm as measured in a 150 mM sodium chloride solution by dynamic light scattering. The size of the particles did not change after 2 days in the 150 mM sodium chloride solution incubated at 40° C.

Example 7

Characterization of Colloidal Suspensions of SPIO Nanoparticles

The colloidal suspensions obtained as the result of the tangential flow filtration were evaluated for stability and zeta potential.

The hydrodynamic diameter ($D_H$) was measured via dynamic light (DLS) scattering using 150 mM NaCl in water as the suspension medium. The purified SPIO suspension from the tangential flow filtration was diluted into 150 mM NaCl in water and passed through a 200 nm filter to remove dust prior to DLS analysis using a Brookhaven ZetaPALS. The dilution was carried out to yield a minimum of 20,000 counts per second during the DLS measurement. The measurements were made shortly after the modified nanoparticles were made. A significant increase in the $D_H$ after storage was an indication that nanoparticles had aggregated and that therefore the particular colloidal suspension was not stable. The results are set forth in Table 1.

TABLE 1

| Nanoparticle Coating | $D_H$ post synthesis | $D_H$ after 18 h in 40 C. saline |
|---|---|---|
| PEG-350 α-hydroxy phosphonate | 10 ± 1 nm | |
| PEG-2000 α-hydroxy phosphonate | 20 ± 1 nm | 22 ± 1 nm |
| PEG-5000 α-hydroxy phosphonate | 20 ± 1 nm | 21 ± 1 nm |
| PEG-10000 α-hydroxyphosphonate | 23 ± 1 nm | 24 ± 1 nm |
| PEG-30000 a-hydroxyphosphonate | 30 ± 1 nm | 30 ± 1 nm |

Example 8

Imaging of Liver Signal Intensity In Vivo by MRI

All procedures involving animals were completed under protocols approved by the GE Global Research Institutional Animal Care and Use Committee. Image data were collected prior to injection of the iron oxide nanoparticle test agent, and then at various time points (e.g., days 1, 2, 5, 7, 21, 28 . . . ) following injection. Test agent was injected through a catheter placed in the lateral tail veins of ~150 g female Lewis rats (Charles River Laboratories, Wilmington, Mass.), and was dosed at 5 mg Fe/kg body weight with the exception of the PEG-30,000 α-hydroxy phosphonate coated agent, which was dosed at 3 mg Fe/kg due to material limitations. The catheter was flushed with saline following the injection.

Imaging was conducted on a clinical 1.5 T GE Signa scanner using a custom-built, ~6 cm solenoid receive RF coil. To prepare for imaging, the rats were anesthetized by placing in an induction chamber filled with 3% isoflurane in oxygen. The prepared animal was then placed within the RF coil and positioned within the bore of the scanner and maintained on 2-3% isoflurane through a nose cone.

A 3D fast gradient echo pulse sequence was employed that allowed collection of images at 12 echo times. The imaging slab was positioned via the graphical prescription interface such that the liver was centered within the transaxial slab and 12 images per slab were collected. The pulse sequence parameters were as follows: pulse sequence: 3D ME fGRE; TE: ranged from 2.7 to 55.2 ms, with 4.7 ms spacing; TR: 146.8 ms; flip angle: 25 degrees; bandwidth: 12.5 MHz; matrix: 192×160; NEX: 1; slice thickness: 1.1 mm; spacing between slices: 1.1 mm; field of view: 9 cm, yielding a voxel size of 0.35×0.35×1.1. The sequence acquisition time was ~2 min.

The imaging data sets were analyzed using a custom software tool (CineTool v8.0.2, GE Healthcare) built upon the IDL platform (IDL v. 6.3, ITT Corp., Boulder, Colo.). In brief, the image analysis tool allowed manual drawing of 3D regions of interest (ROIs) on the liver-containing slices of each series with subsequent calculation of the $T_2^*$ time constant by exponential regression for every voxel within the drawn ROIs. Liver $R_2^*$ values, calculated as the inverse of the $T_2^*$ so determined, are plotted in FIGS. 1 and 2 for the α-hydroxy phosphonate-PEG coated iron oxide nanoparticles of varying PEG molecular weight.

FIG. 1 shows the $R_2^*$ relaxation rate in liver measured via MR imaging longitudinally living rats following intravenous injection of 5 mg Fe/kg of α-hydroxyphosphonate-PEG coated iron oxide nanoparticles. The rate of particle processing in liver, reflected by loss over time of the $R_2^*$ signal, exhibits dependence on the length of the PEG chain of the coating ligand. With a 5000 Dalton MW PEG coating, the liver signal decay is mono-exponential and rapid, returning to baseline within approximately one week. In contrast, particles coated with lower MW PEG (2000 Daltons and lower) exhibit biphasic decay, with liver signal remaining elevated at varied levels for many months. (mean±SD, n≥3)

Liver $R_2^*$ relaxation rate profiles in liver for particles coated with higher MW PEG (5000 Daltons and higher) are shown in FIG. 2. The x-axis is expanded from that in FIG. 1 to show that 3 different particles coated with PEGs of MW 5000, 10,000 and 30,000 Daltons each showed similar profiles exhibiting rapid, mono-exponential declines towards to baseline. The 2000 Dalton PEG-coated particle is also displayed for reference.

Because of the improved liver processing characteristics of the disclosed α-hydroxyphosphonic acid-PEG-modified nanoparticles, the modified nanoparticles are also useful as a source of supplemental iron for the treatment of iron deficiency.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A composition comprising:
nanoparticles to which is adhered an α-hydroxyphosphonate moiety, wherein the at least one alpha-hydroxy phosphonate moiety has the structure of Formula I:

Formula I wherein S is a spacer, L is a linkage between S and R, R is a poly(ethylene glycol), and Z is an alkoxy or hydroxy cap at the ω end of the PEG chain wherein said PEG has a molecular weight greater than 5000 daltons and less than or equal to about 30,000 daltons, and o=0 or 1.

2. The composition of claim 1 wherein S is a direct bond, an unsubstituted or substituted aliphatic or cycloaliphatic group or a heteroaliphatic group.

3. The composition of claim 1 wherein S is a straight chain alkyl group of 1 to 10 carbon atoms in length.

4. The composition of claim 1 wherein L is a direct bond, carbonyl group, ether group, amine group, amide group, ester group, carbamate group, urea group or quaternary amine group.

5. The composition of claim 1, wherein the alpha-hydroxy phosphonate moiety has the structure of Formula II:

Formula II wherein n=1 or 2 and p~114-681.

6. The composition of claim 5, wherein the nanoparticle comprises a transition metal or a transition metal compound.

7. The composition of claim 5, wherein the nanoparticle comprises a paramagnetic material.

8. The composition of claim 6, wherein the transition metal or transition metal compound is selected from the group consisting of iron, manganese, copper, cobalt, nickel, and combinations thereof.

9. The composition of claim 5, wherein the nanoparticle comprises superparamagnetic iron oxide.

10. The composition of claim 9, wherein the iron oxide is doped with another metal.

11. The composition of claim 1, wherein the nanoparticle has an average hydrodynamic diameter $(D_H)$ as determined by dynamic light scattering in 150 mM NaCl water of 15 nm to 100 nm.

12. The composition of claim 1, wherein the nanoparticle has an average hydrodynamic diameter $(D_H)$ as determined by dynamic light scattering in 150 mM NaCl water of 15 nm to 50 nm.

13. The composition of claim 1, wherein the nanoparticle has an average hydrodynamic diameter $(D_H)$ as determined by dynamic light scattering in 150 mM NaCl water of about 20 nm to about 30 nm.

14. The composition of claim 1, wherein said nanoparticle is sufficiently hydrophilic to form a stable aqueous colloidal suspension that exhibits no substantial change in hydrodynamic diameter $(D_H)$ as determined by dynamic light scattering in 150 mM NaCl water after tangential flow filtration and storage for one week at room temperature.

15. A composition suitable for administration to a mammalian subject comprising:
nanoparticles to which are adhered alpha-hydroxy phosphonate moieties; wherein said alpha-hydroxy phosphonate moieties have the structure of Formula I:

wherein S is a spacer, L is a linkage between S and R, R is a poly(ethylene glycol), and Z is an alkoxy or hydroxy cap at the ω end of the PEG chain and o=0 or 1, and said PEG has a molecular weight greater than 5000 daltons and less than or equal to about 30,000 daltons; and a pharmaceutically acceptable carrier or excipient.

16. The composition of claim 15, wherein the alpha-hydroxy phosphonate moieties have the structure of Formula II:

Formula II wherein n=1 or 2 and p~114-681.

17. The composition of claim 15, wherein S is a direct bond, an unsubstituted or substituted aliphatic or cycloaliphatic group, a heteroaliphatic group, or combinations thereof.

18. The composition of claim 15, wherein L is a direct bond, carbonyl group, ether group, amide group, ester group, carbamate group, urea group or combinations thereof.

19. The composition of claim 15, wherein the nanoparticles are suitable for use as an MRI contrast agent.

20. The composition of claim 15, wherein the nanoparticles comprise superparamagnetic iron oxide.

21. The composition of claim 15, wherein the nanoparticles have an average hydrodynamic particle size ($D_H$) between 15 nm and 100 nm in 150 mM NaCl water as determined by dynamic light scattering.

22. The composition of claim 15, wherein the nanoparticles have an average hydrodynamic particle size ($D_H$) between 15 nm and 50 nm in 150 mM NaCl water as determined by dynamic light scattering.

23. The composition of claim 15, wherein the nanoparticles have an average $D_H$ between about 20 nm and about 30 nm.

24. The composition of claim 15, wherein said nanoparticles are sufficiently hydrophilic to form a stable aqueous colloidal suspension that exhibits no substantial change in hydrodynamic diameter ($D_H$) as determined by dynamic light scattering in 150 mM NaCl water after tangential flow filtration and storage for one week at room temperature.

25. The composition of claim 15, wherein the carrier is an isotonic aqueous medium.

26. The composition of claim 15, wherein the carrier is at physiological pH.

27. A method of diagnostic imaging using PEG-substituted alpha-hydroxy phosphonate coated nanoparticles comprising:

subjecting to imaging an individual to whom a nanoparticle composition has been administered, said nanoparticle composition comprising iron oxide nanoparticles to which is adhered an α-hydroxyphosphonate moiety, wherein the α-hydroxy phosphonate moiety has the structure of Formula I:

Formula I wherein S is a spacer, L is a linkage between S and R, R is a poly(ethylene glycol), and Z is an alkoxy or hydroxy cap at the ω end of the PEG chain and o=0 or 1, wherein said PEG has a molecular weight greater than about 5000 daltons and less than or equal to about 30,000 daltons.

28. The method of claim 27, wherein the α-hydroxy phosphonate moiety has the structure of Formula II:

Formula II wherein n=1 or 2 and p~114-681.

29. The method of claim 27, wherein the nanoparticle composition that has been administered to the subject acts as a contrast agent.

30. The method of claim 27, wherein said nanoparticles are administered by inhalation or ingestion.

31. The method of claim 27, wherein said nanoparticles are administered parenterally.

32. The method of claim 27, wherein said nanoparticles are administered by injection or infusion.

33. The method of claim 27, wherein the nanoparticles are implanted into the subject.

34. The method of claim 27, in which the imaging is by magnetic resonance (MR).

35. A method of treating an iron deficiency using PEG-substituted alpha-hydroxy phosphonate coated nanoparticles comprising:

administering to an individual a nanoparticle composition comprising nanoparticles having an iron oxide core to which is adhered an α-hydroxyphosphonate moiety, wherein the α-hydroxy phosphonate moiety has the structure of formula I:

Formula I wherein S is a spacer, L is a linkage between S and R, R is a poly(ethylene glycol), and Z is an alkoxy or hydroxy cap at the ω end of the PEG chain and o=0 or 1, wherein said PEG has a molecular weight greater than about 5000 daltons and less than or equal to about 30,000 daltons.

36. The method of claim 35, wherein the α-hydroxyphosphonate moiety has the structure of formula II Formula II wherein n=1 or 2 and p~114-681.

37. The method of claim 35, wherein the nanoparticle composition that has been administered to the subject acts as a source of bioavailable iron.

38. The method of claim 35, wherein said nanoparticles are administered parenterally.

39. The method of claim 35, wherein said nanoparticles are administered by injection.

40. The method of claim 35, wherein said nanoparticles are administered by infusion.

41. The method of claim 35, wherein the nanoparticles are implanted into the subject.

42. The method of claim 35, wherein the nanoparticles are administered by ingestion.